United States Patent [19]
Padros-Fradera

[11] Patent Number: 5,399,090
[45] Date of Patent: Mar. 21, 1995

[54] DENTAL IMPLANT

[75] Inventor: Alefandro Padros-Fradera, Barcelona, Spain

[73] Assignee: Regent Limited, Georgetown,

[21] Appl. No.: 268,642

[22] Filed: Jun. 30, 1994

[51] Int. Cl.⁶ .................................................. A61C 8/00
[52] U.S. Cl. ........................................ 433/173; 433/174
[58] Field of Search ................. 433/173, 174, 175, 176

[56] References Cited

U.S. PATENT DOCUMENTS

| | | | |
|---|---|---|---|
| 3,672,058 | 6/1972 | Nikoghossian | 433/174 |
| 5,108,288 | 4/1992 | Perry | 433/173 |
| 5,338,197 | 8/1994 | Kwan | 433/174 |

*Primary Examiner*—Cary E. O'Connor
*Attorney, Agent, or Firm*—Michael J. Striker

[57] ABSTRACT

A dental implant for fixing a dental prosthesis comprises a main body implantable in a maxilla and having a central hole formed so that a bolt can pass through the central hole for fixing a dental prosthesis, the main body also having a protuberance with a polygonal cross-section, and a pre-prosthetic collar having a central hole through which the bolt can pass and connectable with the main body, the pre-prosthetic collar having an internal thread, and the protuberance having external edges provided with notches which form a threading for engaging with the internal thread of the pre-prosthetic collar, so that the pre-prosthetic collar is fitted onto the protuberance by screwing without need for additional bolts.

6 Claims, 1 Drawing Sheet

DENTAL IMPLANT

BACKGROUND OF THE INVENTION

The present invention deals with a dental implant to be used as support for fixing a dental prosthesis.

It is known to fit a dental prosthesis by first securing a dental implant to the maxilla, so that the implant acts as a base for fixing the prosthesis once the implant has become integrated into the bone.

In particular bolts for dental implants are known which basically have a generally cylindrically shaped main body provided externally with a screw thread for securing it by screwing it to the maxilla. The main body is usually composed of a metallic material, preferably titanium. A trunco-conical section is preferably arranged at the external end of the main body and is smaller base is joined to the screw thread, while its larger base extends in the form of a prismatic protuberances of preferably hexagonal cross-section and is provided with a threaded axial hole. The protuberance enables the main body to be screwed into the maxilla by a tool such as a spanner.

Also, a removably mountable cap secured to the main body by a fixing bolt screwed into the axial hole of the prismatic protuberance is known. The removably mountable cap is secured after a certain amount of time, i.e. when the implant is firstly fixed in the maxilla. Afterwards, the removably mountable cap is withdrawn and replaced with the dental prosthesis which is joined to the prismatic protuberance of the main body by a bolt screwed into the axial orifice. With this type of dental implant, the fitting of the dental prosthesis requires the prior extraction of the removably mountable cap which, under certain circumstances, may present difficulties with the resulting aggravation for the patient.

Recently, caps snappable onto the prismatic protuberance are being used. They do not need to be extracted in order to fit the prosthesis. However, the fixing of these caps leaves a lot to be desired.

SUMMARY OF THE INVENTION

Accordingly, it is an object of the present invention to provide a dental implant which avoids the disadvantages of the prior art.

In keeping with these objects and with others which will become apparent hereinafter, one feature of the present invention resides, briefly stated, in a dental implant of the above mentioned type in which external edges of the prismatic protuberance of the trunco-conical section of the main body has a plurality of notches forming a threading engageable with an internal thread of a pre-prosthetic collar, the pre-prosthetic collar is provided with a coaxial through hole for passing a bolt therethrough to fit the prosthesis to the implant, and the pre-prosthetic collar is fittable onto the prismatic protuberance by screwing without additional bolts.

When the dental implant is designed in accordance with the present invention, it avoids the disadvantages of the prior art.

In the dental implant in accordance with the present invention the protuberance is formed essentially as a straight prism having the polygonal cross-section.

In the inventive dental implant said main body has a trunco-conical section provided with an external thread for implanting in a maxilla, the protuberance extending from the trunco-conical section, the central hole of the main body extending through the protuberance and partially through the trunco-conical section.

In the dental implant in accordance with the present invention the central hole of the main body is threaded, while the central hole of the pre-prosthetic collar is not threaded, so that the bolt can pass through the central hole of the pre-prosthetic collar and is screwable into the threaded central hole of the main body.

In the dental implant the central hole of the pre-prosthetic collar has a first portion with a diameter dimensioned so that the bolt can pass through the first portion with a clearance, and a second portion provided with the internal thread engageable with the threading of the protuberance, the second portion of the central hole of the pre-prosthetic collar being wider than the first portion of the central hole.

In the dental implant the main body is composed of titanium.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
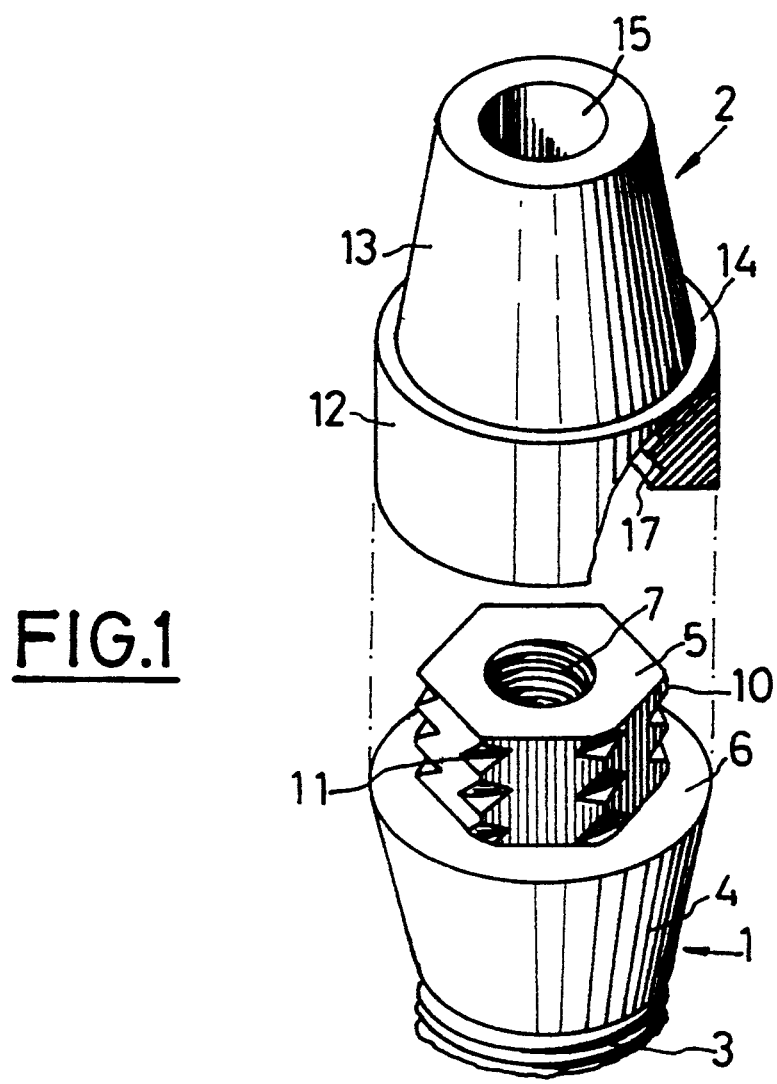
FIG. 1 is a perspective view of a dental implant in accordance with the present invention.

A dental implant in accordance with the present invention has a main body which is identified as a whole with reference numeral 1 and a pre-prosthetic collar which is identified as a whole with reference numeral 2.

For clarity, only a part of the main body 1 is shown in the drawing. The main body 1 has a screw thread 3 for screwing to a maxilla, a coaxial trunco-conical section 4, and a prismatic protuberance 5 extending from the section 4. The prismatic protuberance 5 is coaxial and has a hexagonal cross-section. It is arranged on a larger base of the section 4.

A flat-surfaced intermediate step 6 is defined between the coaxial trunco-conical section 4 and the prismatic protuberance 5. The pre-prosthetic collar 2 is seated on the step 6.

The prismatic protuberance 5 has a central threaded hole 7 which also extends into the trunco-conical section 4. The threaded hole 7 is formed for receiving a bolt 8 for fixing a dental prosthesis 9 to the implant. As can be seen from the drawings, the prismatic protuberance 5 has lateral edges 10 provided with notches 11. The notches 11 are dimensioned and arranged so as to form a screw thread suitable for screwing the pre-prosthetic collar 2 onto the prismatic protuberance.

In the shown exemplary embodiment of the dental implant in accordance with the present invention, the pre-prosthetic collar 2 has two longitudinally joined sections including a first cylindrical section 12 which forms a base of the pre-prosthetic collar 2, and a second trunco-conical section 13. The cylindrical section 12 has an outer diameter which is equal to the diameter of the larger base of the coaxial trunco-conical section 4 of the main body 1. The trunco-conical section 13 has an external smaller base and also a larger base with a diameter which is smaller than the diameter of the first cylindrical section 12. Thereby a flat surfaced stop 14 is defined between the sections 12 and 13. The dental prosthesis 9 is seated on the step 14.

Figure 2:
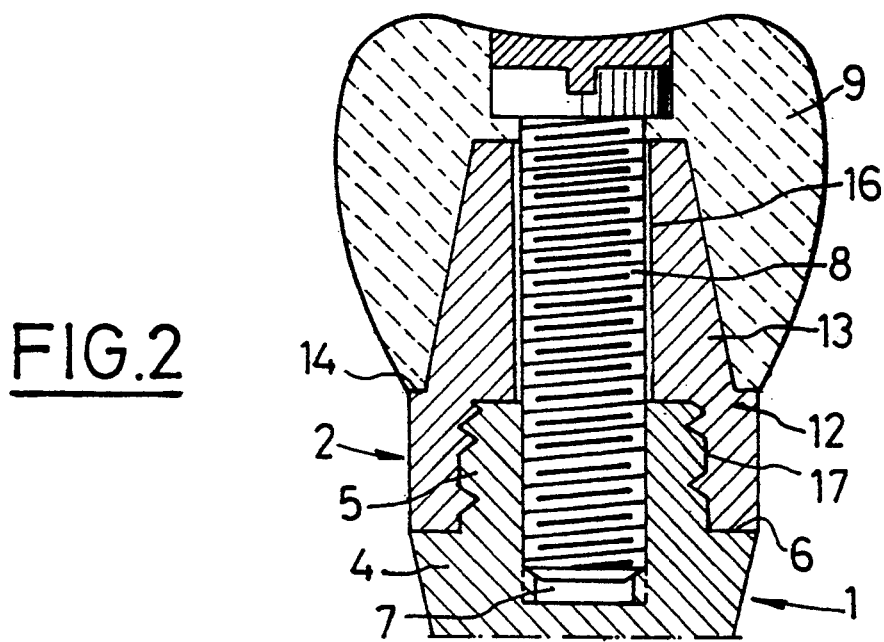
FIG. 2 is a view showing a longitudinal sectional view of the dental implant of FIG. 1 in accordance with the present invention, with a prosthesis fitted to the dental implant.

The pre-prosthetic collar 2 has a coaxial hole 15 with two longitudinally arranged sections. A first external section 16 has a length corresponding to the length of the trunco-conical section 13 and a diameter enabling the bolt 8 for fixing the dental prosthesis 9 to pass with clearance. It also has a second internal section 17 which is threaded in correspondence with the screw thread formed by the notches 11 on the edges 10 of the coaxial prismatic protuberance 5. Thereby the pre-prosthetic collar 2 can be fitted to the prismatic protuberance 5 of the main body 1 by screwing without the use of additional tools as shown in FIG. 2.

It will be understood that each of the elements described above, or two or more together, may also find a useful application in other types of constructions differing from the types described above.

While the invention has been illustrated and described as embodied in a dental implant for supporting dental prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A dental implant for fixing a dental prosthesis, comprising a main body implantable in a maxilla and having a central hole formed so that a bolt can pass through the central hole for fixing a dental prosthesis, said main body also having a protuberance with a polygonal cross-section; and a pre-prosthetic collar having a central hole through which the bolt can pass and connectable with said main body, said pre-prosthetic collar having an internal thread, and said protuberance having external edges provided with notches which form a threading for engaging with said internal thread of said pre-prosthetic collar, so that said pre-prosthetic collar is fitted onto said protuberance by screwing without need for additional bolts.

2. A dental implant as defined in claim 1, wherein said protuberance is formed essentially as a straight prism having said polygonal cross-section.

3. A dental implant as defined in claim 1, wherein said main body has a trunco-conical section provided with an external thread for implanting in a maxilla, said protuberance extending from said trunco-conical section, said central hole of said main body extending through said protuberance and partially through said trunco-conical section.

4. A dental implant as defined in claim 1, wherein said central hole of said main body is threaded, while said central hole of said pre-prosthetic collar is not threaded, so that the bolt can pass through said central hole of said pre-prosthetic collar and is screwable into said threaded central hole of said main body.

5. A dental implant as defined in claim 1, wherein said central hole of said pre-prosthetic collar has a first portion with a diameter dimensioned so that the bolt can pass through said first portion with a clearance, and a second portion provided with said internal thread engageable with said threading of said protuberance, said second portion of said central hole of said pre-prosthetic collar being wider than said first portion of said central hole.

6. A dental implant as defined in claim 1, wherein said main body is composed of titanium.

* * * * *